United States Patent [19]

O'Donnell, Jr.

[11] Patent Number: 5,345,948
[45] Date of Patent: Sep. 13, 1994

[54] METHOD OF PERFORMING TRANSLACTRIMAL LASER DACRYOCYSTORHINOSTOMY

[76] Inventor: Francis E. O'Donnell, Jr., 709 The Hamptons La., Town & Country, Mo. 63017

[21] Appl. No.: 44,163

[22] Filed: Apr. 8, 1993

[51] Int. Cl.$^5$ ............................................. A61B 19/00
[52] U.S. Cl. ......................................... 128/898; 606/4
[58] Field of Search ............................... 128/897–898; 623/4; 606/4–6, 15–18

[56] References Cited

U.S. PATENT DOCUMENTS 4,660,546 4/1987 Herrick et al. ...................... 128/898
5,217,452 6/1993 O'Donnell ........................... 128/898

*Primary Examiner*—Lee S. Cohen
*Assistant Examiner*—John P. Lacyk
*Attorney, Agent, or Firm*—Paul M. Denk

[57] ABSTRACT

A method fo performing dacryocystorhinostomy is provided in which the surgeon inserts a video endoscope into a punctum, through the associated canaliculus and into the lacrimal sac. The surgeon passes a bone cutting laser, connected to a fiber optic bundle, through the other punctum, through the associated canaliculus and into the lacrimal sac. The laser is illuminated through the fiber optic bundle and visualized through the video endoscope. The laser is properly positioned sometime with the help of a transnasal videoendoscope to confirm optimal position relative to nasal structure. The laser is then activated so as to form a full thickness tear draining fistula through the sac and the nasal bone. A tube or stent may be placed to keep the fistula patent or from closure.

12 Claims, 2 Drawing Sheets

METHOD OF PERFORMING TRANSLACRIMAL LASER DACRYOCYSTORHINOSTOMY

BACKGROUND OF THE INVENTION

This invention relates to a method of performing ophthalmological surgery, more specifically, to a method of performing a translacrimal laser dacryocystorhinostomy (DCR).

A substantial number of patients are seen by physicians, particularly ophthalmologists, each year complaining of symptoms indicating a blockage of the lacrimal drainage apparatus, i.e., the tear drainage system of the eye. These symptoms include excessive tears which can flow down the cheeks. Often the symptoms are caused when the volume of tears produced exceeds the normal drainage capacity of the lacrimal system. More commonly, this problem occurs when there is an obstruction in the tear drainage apparatus (obstructive epiphora). A large number of the patients have an anatomical obstruction in the membranous tear drainage passage or a functional defect therein.

Constantly watering eyes is an annoyance and an embarrassment and can cause impaired vision and excoriation of the skin on the cheeks and face. Also, obstructive passages can become infected resulting in contaminated tears which can pose a threat to the patient's vision.

Most patients with obstructive epiphora can be relieved by a surgical procedure wherein a mucosa-lined passageway to the nose is constructed to allow the drainage of the tears.

The most common surgical procedure used to correct the defect is a dacryocystorhinostomy (DCR). Traditional DCR surgery requires making an incision on the side of the nose, suturing the muscles to draw the muscles out of the way, removing sufficient bone from the nose to allow the surgeon to incorporate the lacrimal sac into the nose so that the tears can drain into the nasal passages.

There are several serious complications involved with lacrimal surgery. The most dangerous complication is hemorrhage. Ordinarily, primary hemorrhage is handled by the surgeon during the procedure and is not a long term problem. However, secondary hemorrhage can occur from four to seven days post-op and is usually associated with infection of the mucosa that involves adjacent blood vessels. This complication usually responds to antibiotics. Occasional stitch absesses can develop which also require treatment with antibiotics. Unsightly scars can result from traditional DCR surgery since the surgeon has to make an incision on the side of the nose.

Finally, there can still be a failure to achieve proper drainage despite surgery due to several reasons. First, the surgeon may have performed an inappropriate procedure, usually due to an error in diagnosis. Secondly, the technique of the surgeon may result in failure, due to inadequately marsupialization of the sac to the nose. Re-operation may be required if the surgery fails for any one of the aforestaed complications. Of course, re-operation has its similar attendant risks.

Recently Massaro has described a transnasal method to form a fistula track from the nose to the lacrimal sac using an Argon laser. However, the method has several drawbacks including poor visualization of the intranasal operative field as well as the potential for significant thermal drainage. The argon wavelength is not a very effective bone cutting device. It is therefore, an object of the present invention to provide a method of performing a lacrimal drainage operation using a laser and a video endoscope through the lacrimal system.

Another object of the present invention is to provide a method of performing lacrimal drainage operation does not require skin incision and the associated risk.

Still another object of the present invention is to provide a method of performing a lacrimal drainage operation wherein a laser is passed transcanalicularly to create a full thickness fistula from the lacrimal sac to the nose.

Yet another object of the present invention is to provide a method of performing a lacrimal drainage operation wherein a video endoscope is used to view the operative field.

A further objection of the present invention is to provide a method of performing lacrimal drainage operation using laser technology that is safe and effective, has a low incidence of untord complications and is well suited for its intended purposes. In particular, modified pulsed YAG laser (long pulse duration), Holmium, erbium, or other infrared lasers are better suited for bone cutting.

Another object of this claim is to use a transclacrimal laser to open the naturally occurring drainage route (the nasolarcrimal duct) by perforating any soft tissue or dacryolth obstruction. Another object of this claim is to provide a non-incisional means to revise a failed conventional DCR.

Briefly stated, a method of performing lacrimal drainage surgery is provided wherein a video endoscope is passed from one punctum and is canaliculus into the lacrimal sac. A bone cutting laser with accompanying fiber optic illumination is passed through the other punctum and its associated canaliculus. The laser is activated under direct visualization to create a full thickness fistula from the lacrimal sac into the interior of the nose. Videoendoscopy through the nose can be used to help place the fistual site, avoiding nasal structure or the turbinater. A temporary tube or stent can be passed through the fistula to prevent closure of the fistula.

DESCRIPTION OF THE PREFERRED EMBODIMENT

Figures 1, 2:
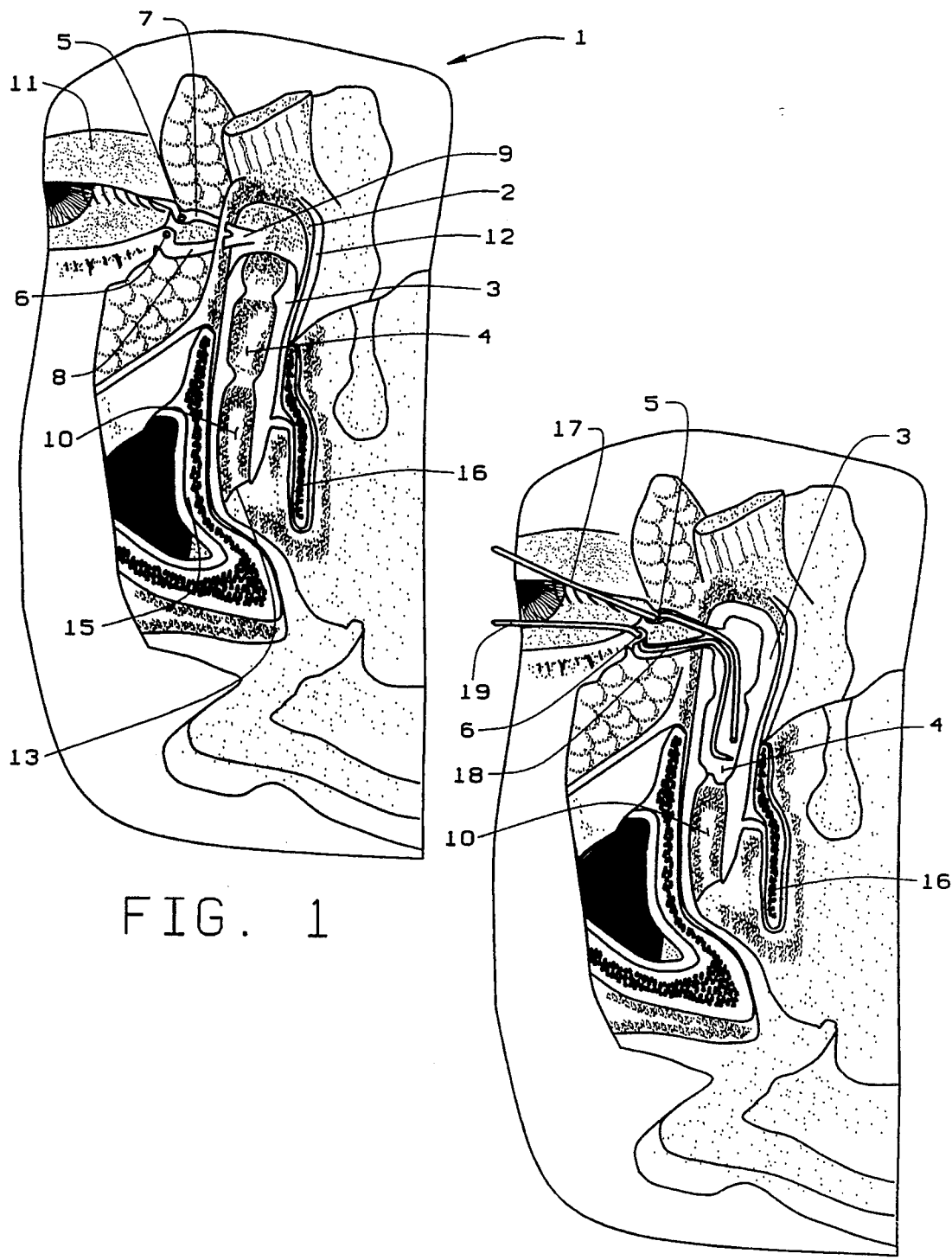
FIG. 1 is a partial schematic illustrating the lacrimal drainage system and associated bony structures.
FIG. 2 is a partial schematic illustrating the lacrimal drainage system and associated bony structures with a video endoscope and a bone cutting laser inserted therein.

An anatomical structure of the lacrimal drainage system is shown generally as reference numeral 1 in FIG. 1. The lacrimal gland 2 is of the tubuloalveolar-type composed of the lacrimal sac 3 surrounding a central canal 4.

The collecting portion of the lacrimal drainage system 1 is composed of the lacrimal sac 3, the puncta 5, 6, the canaliculi 7, 8 and the nasal lacrimal duct 10.

The puncta 5, 6 are slightly elevated, round or slightly oval openings about 3 millimeters in size located on the upper and lower eyelid 11 margins. The canaliculi 7, 8 are tubular-like structures extending from puncta 5, 6, respectively. Canaliculi 7, 8 join to form the common canaliculi 9 which opens into the lacrimal sac 3. Lacrimal sac 3 is located in the medial portion of the orbit of the eye in the lacrimal fossa 12. The lacrimal duct 10 is a downward extension of sac 3 and opens into the inferior nasal meadus 13. The duct is surrounding by bone 15 and the inferior tubinate bone 16.

Figure 3:
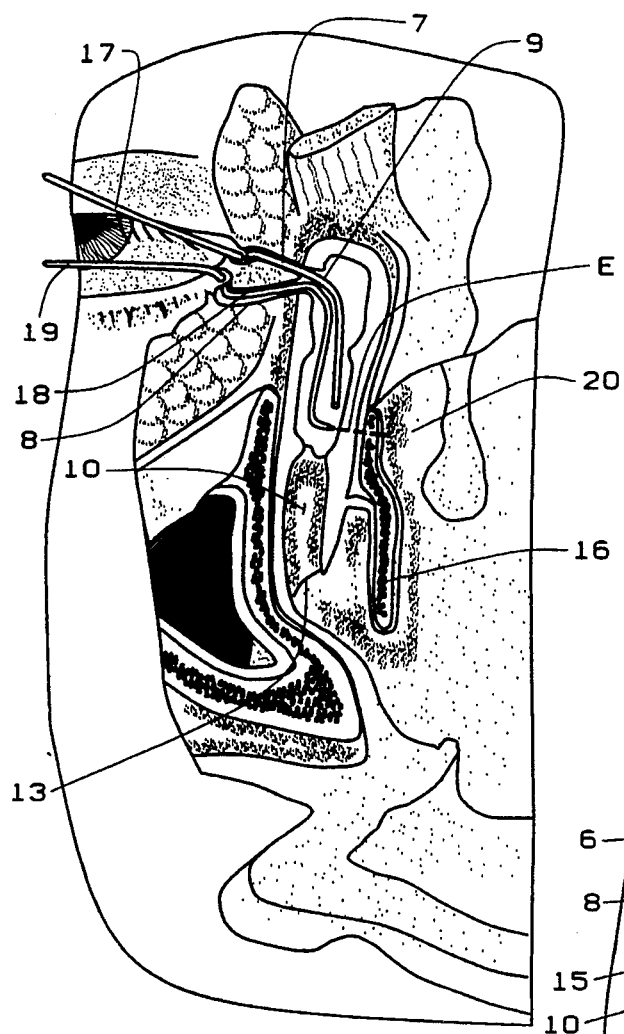
FIG. 3 is a partial schematic similar to FIG. 2 with the laser activated.

Dacryocystitis, a chronic inflamation and infection caused by obstruction of the nasal lacrimal duct 10 or caused by an occlusion of the lacrimal sac 3. Also, spontaneous atresia (closure of a normal anatomical opening) can occur in middle life, especially in women. The surgical method of the present invention, best illustrated in FIGS. 2 and 3, is employed to treat these conditions where the canaliculi 7, 8 are patent.

As shown in FIG. 2, the surgeon (not shown) inserts a video endoscope 17 through punctum 5, through canalula 7, through the common canaliculus 9 through central canal 4 and into the lacrimal duct 10. Video endoscope 17 can be of the type commonly known in the art such as the FVS 1000 (M&M Company, Tokyo Japan). Next, the surgeon inserts a bone cutting laser 18 through punctum 6, through canaliculus 8, through common canaliculus 9, through central canal 4 into the nasal lacrimal duct 10. It should be noted that the bone cutting laser 18 is of a conventional type such as YAG laser (Laser Medical Technology) or the Holmium laser (Sunrise Technologies). Laser 18 is operatively connected to a illuminating fiber-optic bundle 19 and a power source (not shown).

Figure 4:
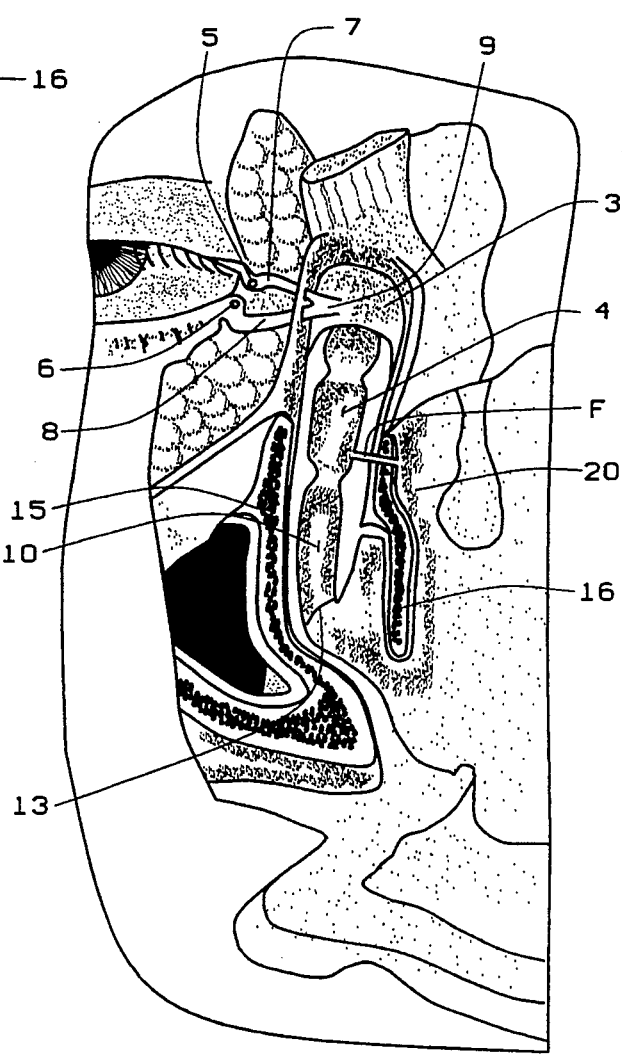
FIG. 4 is a partial schematic illustrating the lacrimal drainage system and associated bony structures illustrating the fistula formed between the lacrimal sac and the interior of the nose.

The surgeon can visualize placement of laser 18 through video endoscope 17 and thus place laser 18 in a proper position before activation. As shown in FIG. 3, the surgeon activates laser 18, causing laser energy E to cut through the sac tissue and bone. The surgeon visualizes the cutting process through the endoscope 17 until a full thickness opening or fistula F (FIG. 4) is formed between the lacrimal duct 10 and the internal antrum 20 of the nose. The surgeon can employ a transnasal videoendoscope to assist in placement of the fistula.

The surgeon withdraws laser 18 from the lacrimal duct and visualizes the operative area as well as fistula F through endoscope 17. When the surgeon determines there is an open, functioning drainage fistula F, he withdraws video endoscope 17. Or, before withdrawing the endoscope, the surgeon can insert a tube or stent in fustula F to keep it open.

The translacrimal laser of this particular invention can also be used to facilitate the opening up of the normal drainage of the normal drainage passageway surrounded by the bone 15, in addition to sustaining the opening of the nasolacrimal duct, possibly using a stent to help maintain patentcy. Furthermore, the laser could be used to remove any dacryostitis (stones), that may exist in the sac or duct. Alternatively, the nasolacrimal duct can be treated with the laser itself, that duct being located at 10, in order to provide the proper drainage.

Numerous variations, within the scope of the appended claims, will be apparent to those skilled in the art in light of the foregoing description and accompanying drawings. For example, various types of lasers can be employed as well as various types of visualizing endoscopes. Also, the position within the lacrimal duct at which the fistual is formed can vary depending upon the anatomical structures of each particular patient. These variations are merely illustrative.

Having thus described the invention, what is claimed and desired to be secured by letters patent is:

1. A method for performing ophthalmological surgery comprising the steps of:
   making a first punctum through the upper eyelid margin to attain access to a first canaliculus;
   passing a video endoscope through the first punctum and through the first canaliculus;
   passing said video endoscope into a lacrimal sac;
   making a second punctum through the lower eyelid margin to attain access to a second canaliculus;
   passing a bone cutting laser through the second punctum and through the second canaliculus;
   passing said bone cutting laser into said lacrimal sac;
   visualizing said laser through said video endoscope;
   positioning said laser towards an inferior turbinae bone;
   activating said laser; and
   forming a full thickness fistula through said lacrimal sac and through said inferior turbinate bone.

2. The method of claim 1 further using the translacrimal laser to remove dacryoliths or perforate a soft tissue obstruction in the nasolacrimal duct to achieve normal drainage.

3. The method of claim 1 wherein the step of passing a video endoscope through a first punctum and through a first canaliculus further comprises a step of passing a FVS 1000 video endoscope through a first punctum and through a first canaliculus.

4. The method of claim 1 wherein said step of passing a laser through a second punctum and through a second canaliculus further comprises the step of passing a laser which has been connected to a fiber optic bundle through a second punctum and through a second canaliculus.

5. The method of claim 1 wherein said laser is a YAG laser.

6. The method of claim 1 further using the translacrimal laser to revise a failed DCR.

7. The method of claim 1 wherein said laser is a Holmium laser.

8. The method of claim 3 wherein said step of visualizing said laser through said video endoscope further comprises the step of illuminating said laser through said fiber optic bundle.

9. A method of performing a translacrimal laser dacryocystorhinostomy comprising the steps of:
   creating a first punctum in the upper eyelid margin to attain access to the canaliculus;
   passing a video endoscope through the first punctum;
   passing said video endoscope through the first canaliculus;
   passing said video endoscope into the lacrimal sac;
   creating a second punctum through the lower eyelid margin to attain access to the second canaliculus;
   passing a bone cutting laser through the second canaliculus;
   passing said bone cutting laser into said lacrimal sac;
   illuminating said laser through a fiber optic bundle;
   visualizing said laser through said video endoscope;
   positioning said laser towards an inferior turbinate bone;
   activating said laser;

forming a full thickness fistula through said lacrimal sac and through said inferior turbinate bone.

10. The method of claim 9 wherein said laser is a YAG laser.

11. The method of claim 9 wherein said laser is a Homium laser.

12. The method of claim 9 further including the step of placing a stent in said full thickness fistual.

* * * * *